(12) United States Patent
Buchanan et al.

(10) Patent No.: US 7,858,833 B2
(45) Date of Patent: *Dec. 28, 2010

(54) PROCESS FOR GENERATING LINEAR ALPHA OLEFIN COMONOMERS

(75) Inventors: John S. Buchanan, Lambertville, NJ (US); Krishnan Sankaranarayanan, South Riding, VA (US); Milind B. Ajinkya, Oakton, VA (US); Stephen M. Wood, Sterling, VA (US); Anastasios Skoulidas, Bristow, VA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 1082 days.

This patent is subject to a terminal disclaimer.

(21) Appl. No.: 11/346,652

(22) Filed: Feb. 3, 2006

(65) Prior Publication Data

US 2007/0185358 A1    Aug. 9, 2007

(51) Int. Cl.
*C07C 2/24* (2006.01)
(52) U.S. Cl. .................. 585/513; 585/510; 585/511; 585/512; 585/517; 585/520; 585/521; 585/523
(58) Field of Classification Search .................. 585/523, 585/530, 510, 511, 512, 513, 517, 520, 521
See application file for complete search history.

(56) References Cited

U.S. PATENT DOCUMENTS 4,511,746 A    4/1985 Miller (Continued)

FOREIGN PATENT DOCUMENTS

EP    668 106    8/1995

(Continued)

OTHER PUBLICATIONS

J.T. Dixon et al., "Advances in Selective Ethylene Trimerisation—A Critical overview," Jrnl. of Organometallic Chemistry, vol. 689, 2004, pp. 3641-3668.

(Continued)

*Primary Examiner*—Glenn A Caldarola
*Assistant Examiner*—Bradley Etherton
(74) *Attorney, Agent, or Firm*—Jamie L. Sullivan

(57) ABSTRACT

The present invention relates to a method for preparing linear alpha olefin comonomers, such as 1-butene, 1-hexene or 1-octene, from ethylene monomer. The comonomer generated is stored on site for use in a subsequent process, such as a polyethylene polymerization reactor. The method includes the steps of feeding an ethylene monomer, and a catalyst in a solvent to one or more comonomer synthesis reactors; reacting the ethylene monomer and the catalyst in solvent under reaction conditions to produce an effluent stream comprising unreacted ethylene monomer, a catalyst in a solvent, and comonomer; passing the effluent stream to one or more downstream gas/liquid phase separators to form a gas stream of unreacted ethylene monomer, and a liquid stream of comonomer, and catalyst in a solvent; recycling to the one or more comonomer synthesis reactors the unreacted ethylene monomer and a portion of the liquid stream; and storing a remaining portion of said liquid stream for subsequent processing of the comonomer. Some of the benefits of the method include process simplification and reduced capital and operating costs from, inter alia, not having to recover ethylene in high purity nor separate catalyst from comonomer.

36 Claims, 5 Drawing Sheets

Process Schematic for the Production of 1-Butene with Isopentane as a Solvent at 800 psia

U.S. PATENT DOCUMENTS

| | | |
|---|---|---|
| 5,000,840 A | 3/1991 | Anthes et al. |
| 5,382,738 A | 1/1995 | Reagen et al. |
| 5,451,645 A | 9/1995 | Reagen et al. |
| 5,523,507 A | 6/1996 | Reagen et al. |
| 5,541,270 A | 7/1996 | Chinh et al. |
| 5,543,375 A | 8/1996 | Lashier et al. |
| 5,563,312 A | 10/1996 | Knudsen et al. |
| 5,859,303 A | 1/1999 | Lashier |
| 6,274,783 B1 | 8/2001 | Gildert et al. |
| 6,423,791 B1 | 7/2002 | Kral |
| 6,800,702 B2 | 10/2004 | Wass |
| 7,687,672 B2 * | 3/2010 | Buchanan et al. ............ 585/326 |

FOREIGN PATENT DOCUMENTS

| | | |
|---|---|---|
| WO | WO 99/19280 | 4/1999 |
| WO | WO 2004/056478 | 7/2004 |
| WO | WO 2004/056479 | 7/2004 |

OTHER PUBLICATIONS

S. Naqvi, "1-Hexene From Ethylene by the Phillips Trimerization Technology," SRI Consulting PEP Review 95-1-8, http://www.sriconsulting.com/PEP/Reports/Phase_95/RW95-1-8/RW95-1-8.html.

* cited by examiner

Process Schematic for the Production of 1-Hexene with 1-Hexene as a Solvent

Process Schematic for the Production of 1-Hexene with Toluene as a Solvent

Process Schematic for the Production of 1-Hexene with Isopentane as a Solvent at 800 psia Process Schematic for the Production of 1-Butene with Isopentane as a Solvent at 800 psia Process Schematic for the Production of 1-Hexene with Isopentane as a Solvent and Polymer Grade Feed

PROCESS FOR GENERATING LINEAR ALPHA OLEFIN COMONOMERS

FIELD OF THE INVENTION

The present invention relates to the field of chemical reaction and separation processes. It more particularly relates to an improved process for generating linear alpha olefin comonomers from monomer. Still more particularly, the present invention relates to improved process for making 1-butene, 1-hexene and other comonomers from ethylene.

BACKGROUND

Olefin polymerization, especially ethylene polymerization, can benefit from the addition of longer-chain comonomers, such as 1-butene, 1-hexene, and 1-octene, to produce linear low density polyethylene (LLDPE). LLDPE produced from 1-butene, 1-hexene and 1-octene accounts for a large percentage of the polyethylene resin market. In general, polyethylene plants buy butene, hexene and octene, which are produced in separate plants that typically produce a range of even-numbered alpha olefins from ethylene. It can be expensive to purchase these materials, and they add to the complexity of transport, storage and handling. An attractive alternative is to make the comonomer directly from the ethylene at the site where they will be used, if this can be done cleanly and economically.

The review article "Advances in selective ethylene trimerisation—a critical review" by Dixon et al. (J. Organometallic Chemistry 689 (2004) 3641-3668), herein incorporated by reference in its entirety, describes many different catalysts for trimerization. These catalyst systems contain chromium, and with particular ligands, such as aromatic species (e.g. pyrrolyl) or multidentate heteratomic species. The chromium catalysts are typically activated by alkylaluminum and/or alkyaluminoxane activators. The article also describes group 4 and 5 early transition metals, such as Zr, V, Ta and Ti, and group 8 late transition metals, such as Ni, for showing some activity in trimerization.

Phillips has developed chromium-based catalysts that are selective towards making 1-hexene from ethylene. The major byproduct appears to be 1-decene. SRI Consulting PEP Review 95-1-8 entitled "1-Hexene From Ethylene By the Phillips Trimerization Technology," available on-line at http://www.sriconsulting.com/PEP/Reports/Phase_95/RW95-1-8/RW95-1-8. html, herein incorporated by reference in its entirety, describes the Phillips standalone process for making 1-hexene based on Phillips trimerization technology. In this process, ethylene and a homogeneous catalyst in a solvent are fed to a reactor. The reactor is a stirred tank with heat removal coils. This reactor operates at 115 deg. C. and 49 kg/cm2 (~700 psia), and converts about 75% of the ethylene fed. This reactor is 42,300 gal (5655 ft3). A spare reactor is provided, since waxy buildup on the cooling coils may necessitate lengthy shutdowns for cleaning. The feed is approximately 29,000 lb/hr cyclohexane solvent (with catalyst) plus 36,000 lb/hr ethylene (27,000 fresh feed and 9,000 recycle). It is estimated that the resident time in the reactor is on average 4 to 5 hours. Selectivity in the SRI process by weight is about 93% to 1-hexene, 1% to other C6s, 1% to octenes, and 5% to decenes. The effluent from the reactor is contacted with octanol to kill the catalyst from further reaction. The effluent then goes to an ethylene column where unconverted ethylene is taken overhead and recycled to the reactor. Because ethylene is so volatile, an expensive cryogenic column must be used. Four more distillation columns follow to remove hexene, cyclohexane solvent, octene, and decene. Some of these are run under vacuum, which again makes for expensive hardware and operations. The bottoms from the decene tower is a small stream containing mainly octanol and deactivated catalyst. This stream is treated with caustic and then with acid to remove the catalyst by precipitation and by solution in an aqueous phase, which is separated from the organic phase containing the octanol. Octanol may then be recycled.

U.S. Pat. No. 5,382,738 to Reagen et al., herein incorporated by reference in its entirety, discloses catalyst systems comprising inorganic oxides, modified with a metal alkyl and an unsaturated hydrocarbon, which can be used to support a metal source, such as, for example, chromium, and a pyrrole-containing compound. The resultant catalyst systems can be used to oligomerize and/or trimerize olefins via a slurry process.

U.S. Pat. No. 5,451,645 to Reagen et al., herein incorporated by reference in its entirety, discloses novel chromium-containing compounds prepared by forming a mixture of a chromium salt, a metal amide, and an ether. These novel chromium-containing, or chromium pyrrolide compounds, with a metal alkyl and an unsaturated hydrocarbon, can be used as a co-catalyst system in the presence of an olefin polymerization catalyst system to produce a comonomer in-situ with trimerization.

U.S. Pat. No. 5,543,375 to Lashier et al., herein incorporated by reference in its entirety, discloses a process to stabilize and/or reactivate an olefin production catalyst system, which comprises contacting an olefin production catalyst system, either before or after use, with an aromatic compound.

European Patent No. 0 668 106 to Freeman et al., herein incorporated by reference in its entirety, discloses a process which will effectively deactivate, inhibit, and/or "kill" an olefin production catalyst, and halt polymer production in an olefin production process. It further provides for a process which can remove an olefin production catalyst from the product stream, and recover catalyst by-products for recycle, and/or recovery.

A need exists for an improved process to generate linear alpha olefin comonomers from monomer. More particularly, a need exists for a reaction and separation process to generate 1-butene, 1-hexene, or 1-octene from ethylene monomer for subsequent isolation or storage prior to being used in a polymerization reactor or other chemical process requiring such comonomer.

SUMMARY OF THE INVENTION

It has been discovered that it is possible to selectively make 1-butene, 1-hexene and other linear alpha olefin comonomers from ethylene monomer via a simpler and less expensive process.

According to the present disclosure, an advantageous method for preparing linear alpha olefin comonomers from ethylene monomer comprises the following steps: providing one or more comonomer synthesis reactors configured in series, and one or more downstream gas/liquid phase separators configured in series; feeding an ethylene monomer, and a catalyst in a solvent to the one or more comonomer synthesis reactors; reacting in the one or more comonomer synthesis reactors the ethylene monomer and the catalyst in solvent under reaction conditions to produce an effluent stream comprising unreacted ethylene monomer, the catalyst in a solvent, and comonomer; passing the effluent stream to the one or more downstream gas/liquid phase separators to form a gas stream of the unreacted ethylene monomer, and a liquid stream of the comonomer and the catalyst in a solvent; recycling to the one or more comonomer synthesis reactors the unreacted ethylene monomer and a portion of the liquid stream; and storing a remaining portion of the liquid stream for subsequent processing of the comonomer; wherein the comonomer is selected from the group consisting of 1-butene, 1-hexene, 1-octene, 1-decene and mixtures thereof, and is similar in composition to the solvent.

A further aspect of the present disclosure relates to an advantageous method for preparing linear alpha olefin comonomers from ethylene monomer, which comprises the following steps: providing one or more comonomer synthesis reactors configured in series, one or more downstream gas/liquid phase separators configured in series, and one or more distillation columns configured in series; feeding an ethylene monomer, and a catalyst in a solvent to the one or more comonomer synthesis reactors; reacting in the one or more comonomer synthesis reactors the ethylene monomer and the catalyst in solvent under reaction conditions to produce an effluent stream comprising unreacted ethylene monomer, the catalyst in a solvent, and comonomer; passing the effluent stream to the one or more downstream gas/liquid phase separators to form a gas stream of the unreacted ethylene monomer, and a liquid stream of the comonomer and the catalyst in a solvent; passing the liquid stream of the comonomer and the catalyst in a solvent to the one or more distillation columns to separate the comonomer from the catalyst in a solvent; recycling to the one or more comonomer synthesis reactors the unreacted ethylene monomer and the catalyst in a solvent; and storing the comonomer for subsequent processing; wherein the comonomer is selected from the group consisting of 1-butene, 1-hexene, 1-octene, 1-decene and mixtures thereof.

Another aspect of the present disclosure relates to an advantageous method for preparing linear alpha olefin comonomers from ethylene monomer, which comprises the following steps: providing a combination comonomer synthesis reactor and gas/liquid phase separator into a single vessel; feeding an ethylene monomer, and a catalyst in a solvent to the combination comonomer synthesis reactor and gas/liquid phase separator; reacting in the combination comonomer synthesis reactor and gas/liquid phase separator the ethylene monomer and the catalyst in solvent under reaction conditions to produce an effluent stream comprising a gas stream of unreacted ethylene monomer and a liquid stream of comonomer and catalyst in a solvent; recycling to the combination comonomer synthesis reactor and gas/liquid phase separator the gas stream and a portion of the liquid stream; and storing a remaining portion of the liquid stream for subsequent processing of the comonomer; wherein the comonomer is selected from the group consisting of 1-butene, 1-hexene, 1-octene, 1-decene and mixtures thereof.

Numerous advantages result from the advantageous method of preparing linear alpha olefin comonomers from ethylene monomer disclosed herein and the uses/applications therefore.

For example, in exemplary embodiments of the present disclosure, the disclosed method for preparing 1-butene, 1-hexene and other linear alpha olefin comonomers from ethylene monomer provides for substantial capital and operational cost savings over a conventional standalone process for manufacturing comonomer.

In a further exemplary embodiment of the present disclosure, the disclosed method for preparing 1-butene, 1-hexene and other linear alpha olefin comonomers from ethylene monomer provides for a simpler process through the elimination of one or more separation columns.

In a further exemplary embodiment of the present disclosure, the disclosed method for preparing 1-butene, 1-hexene and other linear alpha olefin comonomers from ethylene monomer provides for the capability to produce both 1-butene and 1-hexene through catalyst selection.

In a further exemplary embodiment of the present disclosure, the disclosed method for preparing linear alpha olefin comonomers from ethylene monomer provides for high selectivity and activity through trimerization catalyst selection.

In a further exemplary embodiment of the present disclosure, the disclosed method for preparing linear alpha olefin comonomers from ethylene monomer eliminates the need to recover unreacted ethylene monomer in high purity.

In a further exemplary embodiment of the present disclosure, the disclosed method for preparing linear alpha olefin comonomers from ethylene monomer permits the discharge of deactivated catalyst with comonomer product.

These and other advantages, features and attributes of the disclosed method for preparing 1-butene, 1-hexene and other linear alpha olefin comonomers from ethylene monomer of the present disclosure and their advantageous applications and/or uses will be apparent from the detailed description which follows, particularly when read in conjunction with the figures appended hereto.

BRIEF DESCRIPTION OF THE DRAWINGS

To assist those of ordinary skill in the relevant art in making and using the subject matter hereof, reference is made to the appended drawings, wherein.

DETAILED DESCRIPTION OF THE INVENTION

Figure 1:
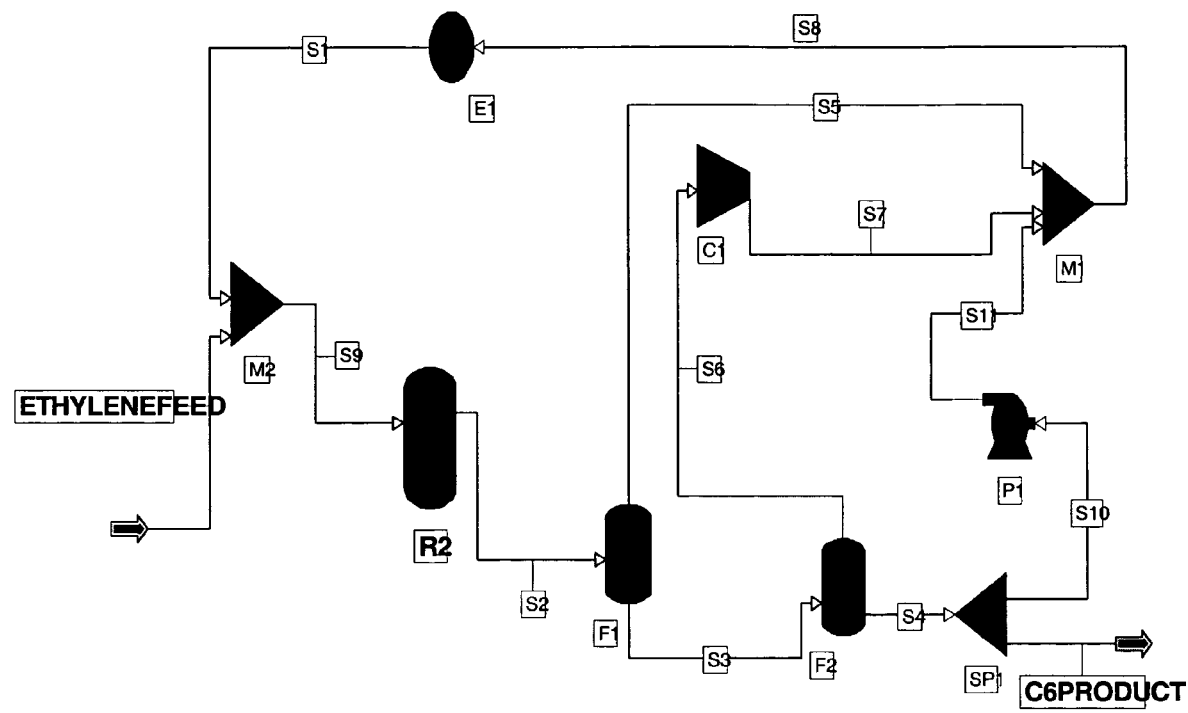
FIG. 1 depicts an exemplary process schematic of the process of the present invention for generating 1-hexene with 1-hexene as a solvent.

The present invention relates to an improved process for generating long-chain linear alpha olefin comonomers (e.g. 1-butene, 1-hexene, 1-octene) from ethylene monomer. The disclosed method of preparing 1-butene, 1-hexene and other linear alpha olefin comonomers from ethylene monomer prior to the polymerization reactor or other chemical process where it will be used greatly simplifies the comonomer synthesis process. The method of the instant invention is compatible with a Phillips-type trimerization catalyst, but is also useful with other homogeneous or heterogeneous selective oligomerization catalysts. A novel feature of the disclosed method of preparing 1-butene, 1-hexene and other linear alpha olefin comonomers from ethylene monomer is that ethylene is not recovered in high purity, which eliminates the need for a cryogenic distillation column and the associated capital and operating costs. Unconverted ethylene may then be recycled to the comonomer synthesis reactor, or sent on to another process, for example, a subsequent polyethylene polymerization process.

Another advantage of the method of the instant invention of preparing 1-butene, 1-hexene and other linear alpha olefin comonomers from ethylene monomer is that an elaborate on-site catalyst separation and disposal is not needed because the residual catalyst may pass with the comonomer for subsequent processing. A further advantage of the method of the instant invention of preparing 1-butene, 1-hexene and other linear alpha olefin comonomers from ethylene monomer is that a small amount of a soluble or slurry catalyst that is sufficiently active may be utilized, such that it can be added in only small amounts. After deactivation, the catalyst can then be discharged with the comonomer product and incorporated into the final polymeric product.

In one exemplary embodiment, the comonomer synthesis reactor is separate from the gas/liquid phase separator, which permits independent control of reaction and separation conditions. In this particular embodiment, ethylene and catalyst in a solvent are fed separately to a comonomer synthesis reactor. The purity of the ethylene monomer feed may vary, but is preferably greater than 80% ethylene, more preferably greater than 99% ethylene, and even more preferably greater than 99.8% pure. The reactor temperature and pressure are controlled to provide for acceptable reaction rates and selectivities, as well as to provide for phase separation.

Catalyst selection permits the capability to produce either predominately 1-butene, 1-hexene, or 1-octene. Catalysts suitable for the present invention are those that comprise a reactive transition metal source catalytically able to selectively trimerize or tetramerize olefins. Exemplary metal sources include, but are not limited to, chromium, vanadium, tantalum, and titanium. Exemplary catalyst types include, but are not limited to, chromium, vanadium, tantalum and titanium trimerization and/or tetramerization catalysts. Preferably the catalytic system comprises a titanium source, more preferably a tantalum source and even more preferably a chromium source for improved catalyst activity and selectivity.

If a chromium source is used, one or more organic ligands may also be present in addition to any inorganic ligands, wherein the oxidation state of the chromium is from 0 to 6. Exemplary organic ligands are organic radicals having from 1 to 20 carbon atoms per radical, which are selected from the group consisting of alkyl, alkoxy, ether, ester, ketone, phosphine and/or amine. The organic ligands may also include heteroatoms. The organic radicals may be straight chained or branched, cyclic or acyclic, aromatic or aliphatic and any combination may be present in the metal complex. The organic radical may include multiple heteroatoms that are linked by bridging groups to provide for multidentate complexation with the chromium source.

Preferred organic radicals include "pyrrole-containing" compounds. For the purposes of this invention "pyrrole-containing" compounds refers to those that include a pyrrole molecular fragment or a derivative of hydrogen pyrrolide, i.e. pyrrole ($C_4H_5N$). Non-limiting examples of "pyrrole-containing" compounds include 2,3-dimethylpyrrole, 2,5-dimethylpyrrole, 2,4-dimethyl-3-ethylpyrrole, 2-acetylpyrrole, 3-acetyl-2,5-dimethylpyrrole and ethyl-3,5-dimethyl-2-pyrrolecarboxylate.

Bridging organic radicals of the present invention include those with one or more phosphorous heteroatoms such as PNP ligands. Non-limiting examples include (2-methyloxyphenyl)$_2$PN(methyl)P(2-methyoxyphenyl)$_2$, (3-methyloxyphenyl)$_2$PN(methyl)P(3-methyoxyphenyl)$_2$, (4-methyloxyphenyl)$_2$PN(methyl)P(4-methyoxyphenyl)$_2$, (2-methyloxyphenyl)$_2$PN(ethyl)P(2-methyoxyphenyl)$_2$, (2-methyloxyphenyl)$_2$PN(isopropyl)P(2-methyoxyphenyl)$_2$, (2-methyloxyphenyl)$_2$PN(methyl)P(3-methyoxyphenyl)$_2$, (2-methyloxyphenyl)$_2$PN(methyl)P(4-methyoxyphenyl)$_2$, (4-fluorophenyl)$_2$PN(methyl)P(4-fluorophenyl)$_2$, and (2-fluorophenyl)$_2$PN(benzyl)P(2-fluorophenyl)$_2$.

Bridging organic radicals of the present invention also include those with a hydrocarbon bridge between the phosphorous heteroatoms. Non-limiting examples include 1-(2-methyoxyphenyl)(phenyl)phosphino-2-(2-methyoxyphenyl)(phenyl)phosphinoethane, 1-di(3-methyoxyphenyl)phosphino-2-(2-methyoxyphenyl)(phenyl)phosphinoethane, 1-(2-methyoxyphenyl)(phenyl)phosphino-3-(2-methyoxyphenyl)(phenyl)phosphinopropane, 1-(4-methyoxyphenyl)(phenyl)phosphino-2-(4-methyoxyphenyl)(phenyl)phosphinopropane, 1-(2-methyoxyphenyl)(phenyl)phosphino-2-(2-methyoxyphenyl)(phenyl)phosphinopropane, and 1-diphenylphosphino-2-(2-fluorophenyl)(phenyl)phosphinoethane.

The catalyst system may also include an activator. The activator may be any compound that generates an active catalyst when combined with the transition metal compound and the organic and/or inorganic ligand. Exemplary compounds for activators include, but are not limited to, organoaluminum compounds, organoboron compounds, organic metal salts, and inorganic acids and salts. Preferred activators include alkylaluminum compounds, such as triethylaluminum, trimethylaluminum, triisobutylaluminum and alkylaluminoxanes. Preferred alkylaluminoxanes include methylaluminoxane, ethylaluminoxane and modified alkylaluminoxanes, such as modified methylaluminoxane (MMAO). Ratios of the aluminum activator to the transition metal may be from 1:1 to 10,000:1, preferably from about 1:1 to 5000:1, more preferably from about 1:1 to 1000:1 and even more preferably from about 1:1 to 500:1.

With regard to catalyst solvent, there is flexibility as far as what catalyst solvent may be used. Exemplary solvents include, but are not limited to, the comonomer product (e.g. 1-butene, 1-hexene, 1-octene), C4+ paraffins (e.g. isopentane, isobutane), cycloparaffins, and aromatics (e.g. toluene). If the catalyst is in the form of an immobilized or fixed bed, it may not require additional extraneous solvent. In another exemplary embodiment, the catalyst to the comonomer synthesis reactor may be provided in the form of an immobilized or fixed bed, hence eliminating the need for a solvent altogether.

The comonomer synthesis reactor may take various forms, including but not limited to, a stirred tank, a longer, thinner tube-like contactor or a bubble column. In an alternative embodiment, two or more comonomer synthesis reactors are configured in series. An advantage of series reactors is more thorough utilization of the catalyst, i.e. less nearly-fresh catalyst will get discharged with the product. Heat exchange capacity is also incorporated in the reactor or in a pumparound loop, to limit the exotherm. Where waxy buildup is an issue, spare heat exchangers may also be provided. Depending on the operating pressure of the reactor, the amount of the ethylene dissolved in the catalyst solvent may also be controlled, which adds flexibility in the design of the reactor and the process as a whole.

Comonomer synthesis reaction conditions of the instant invention are selected and controlled to yield from about 40 to about 95% conversion of feed ethylene, and more preferably from about 60 to about 90% conversion of feed ethylene. For some of the chromium catalysts disclosed in U.S. Pat. No. 5,543,375, a range of reaction conditions are disclosed, which are herein incorporated by reference. One exemplary, but non-limiting set of reactor conditions is a temperature from about 80-150° C., and a pressure from about 300-900 psi. A preferred range of reactor temperature with an ethylene monomer is from about 60-110° C. Reaction conditions may be tuned to obtain desired phase separations as well as reactivity. In addition, reactor residence time is flexible, and may be chosen to provide a desired level of ethylene conversion. The residence time is a function of the type and amount of the catalyst utilized. In one exemplary embodiment when utilizing the chromium type catalysts disclosed in U.S. Pat. No. 5,543,375, the average residence time ranges from about 30 minutes to about 4 hours for a backmixed or pumparound reactor where most of the catalyst in the reactor at a given time is not "fresh," but has been circulating around for some time, and has become partially deactivated.

The effluent from the comonomer synthesis reactor is directed to a gas/liquid phase separator where most of the ethylene goes overhead for recycle to the reactor or to a separate process. A catalyst deactivator may be added to the effluent from the reactor to minimize further reactions in downstream equipment. Exemplary catalyst deactivators include, but are not limited to, water and alcohol. Exemplary gas/liquid phase separator types include, but are not limited to, a simple knockout vessel, flash drum or other single or multi-stage phase separators. The gas/liquid phase separator may also include some trays or packing in the zone where vapor is going up, with reflux. The ethylene stream exiting from the gas/liquid phase separator may be pressurized via a compressor or blower prior to being fed back to the comonomer synthesis reactor or to another separate process.

In an alternative embodiment, two or more gas/liquid phase separators are configured in series to further refine the separation of ethylene monomer for linear alpha olefin comonomer. In another alternative embodiment, some ethylene is added to the gas/liquid phase separator below the feed entrance point to strip out 1-hexene from the down-flowing solvent. In another alternative embodiment, the ethylene recycle is dissolved in the recycled solvent at low temperatures. This configuration allows for a simple pump to pressurize the feed mixture instead of a more expensive compressor or blower.

The liquid bottoms from the gas/liquid phase separator, containing catalyst, 1-hexene, other comonomers (octene, and decene), and catalyst solvent, may then be conveyed to a distillation column. In a preferred embodiment, the catalyst is so selective that the amounts of C8-C10 byproducts produced are negligible, and so active that it can be diluted and disposed of in the hexene product. If these conditions are satisfied, the distillation column may function to separate the remaining ethylene from 1-hexene. The ethylene may then be recycled to the comonomer synthesis reactor, and the 1-hexene (containing spent catalyst) is discharged as product from the bottom of the column. In one exemplary embodiment where a very active and very selective catalyst is utilized to produce 1-hexene, a light catalyst solvent may be used such that 1-hexene is collected as the bottom of the distillation column in very high purity, while the catalyst solvent and the ethylene from the overhead are recycled back to the comonomer synthesis reactor.

In another exemplary embodiment where separation between 1-hexene and heavier products is required in addition to the ethylene/hexene separation, a single distillation column may be utilized by making it a divided-wall type column. In this configuration, the catalyst may be discharged with the heavy products. In another exemplary embodiment, a small post-column or other separation process is utilized to separate the catalyst from the heavy products, such that the catalyst may be mixed in with the 1-hexene for disposal. In addition, deactivation of the catalyst, may be utilized, for example, with the use of water.

In another alternative embodiment of the instant invention, the comonomer synthesis reactor and gas/liquid separator are combined into a single vessel for a classic catalytic distillation column, if compatible temperature and pressure can be found, and if sufficient residence time can be provided for reaction. This further simplifies the process complexity and the reduces costs associated with capital equipment and operating costs.

The linear alpha comonomer liquid product stream (1-butene, 1-hexene, 1-octene) resulting from the method of the instant invention is stored in tanks or other type of storage vessel prior to being transported to a subsequent process for further processing. The linear alpha olefin comonomers produced via the process of the instant invention may be used as the comonomer input of a polyolefin polymerization process, and a variety of other applications.

Applicants have attempted to disclose all embodiments and applications of the disclosed subject matter that could be reasonably foreseen. However, there may be unforeseeable, insubstantial modifications that remain as equivalents. While the present invention has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description The following simulated examples illustrate the present invention and the advantages thereto without limiting the scope thereof. The examples are based upon computer based simulations of the input streams and process conditions utilized for each of the exemplary process flow schematics illustrated.

EXAMPLES

For the purposes of the figures which follow in the simulated examples, "S" designates flow stream, "R" designates reactor, "F" designates gas/liquid phase separator, "C" designates compressor or blower, "M" designates mixing element, "P" designates pump, "SP" designates flow splitter, "E" designates heat exchanger, and "T" designates distillation column or tower. The number which follows each of the designations signifies the number of such element within the respective process schematic.

In examples 1-4, a 100% pure ethylene feed is utilized assuming 100% selectivity to produce an alpha-olefin product (either 1-butene or 1-hexene). These idealized conditions were selected for the purpose of determining equipment needs. In practice, the ethylene feed would be less than 100% pure (preferably 98.0-99.9% pure), and reaction selectivity would be less than 100% (e.g. 90-98%). In example 5, a polymer grade ethylene feed (99.9% ethylene and 0.1% ethane) is utilized with a reaction selectivity of 98% 1-hexene, 0.4% 1-octene and 1.6% C10 (1-decene and internal decenes).

Simulation Example 1

1-Hexene Product as a Catalyst Solvent

An exemplary process schematic using the 1-hexene product as the solvent is shown in FIG. 1. The ethylene feed is 100% ethylene while the reaction selectivity to 1-hexene is 100%. The feed is mixed with a recycled ethylene and 1-hexene stream S1 and is fed to reactor R2. The reactor R2 is operated at 90° C. and 400 psia and is sized to achieve 60% per pass conversion of ethylene. The product stream from the reactor S2 is separated from the unconverted ethylene using two flash drums F1, F2 operated at 400 and 14.96 psia respectively. The gas outlet S6 of the second flash drum F2 is then recompressed at 400 psia using a compressor C1 and recycled back to the reactor R2. The liquid stream S4 from the second flash drum F2, which includes >99.5% 1-hexene, is split into two streams, S10 and C6PRODUCT, using a flow splitter SP1. The S10 hexene stream is recycled acting as the catalyst solvent in comonomer synthesis process. Homogeneous or slurry catalyst leaves with the C6PRODUCT stream. A summary listing of stream flow rates and compositions is shown in Table 1. If conversion is increased to 90%, the ethylene concentration in the reactor product stream S2 is sufficiently low such that S2 becomes a single phase (liquid). In this case the first flash drum F1 can be eliminated, which further simplifies the process.

TABLE 1

Flow Rates and Compositions

|  | Rate (lb/hr) | Ethylene | 1-Hexene |
|---|---|---|---|
| Ethylene Feed | 33700 | 100% |  |
| Reactor Outlet | 89406 | 23.30% | 76.70% |
| 1-Hexene Product | 33696 | 0.80% | 99.20% |
| Recycle | 55706 | 18% | 82% |

Simulation Example 2

1-Hexene Product with Toluene as a Catalyst Solvent

Figure 2:
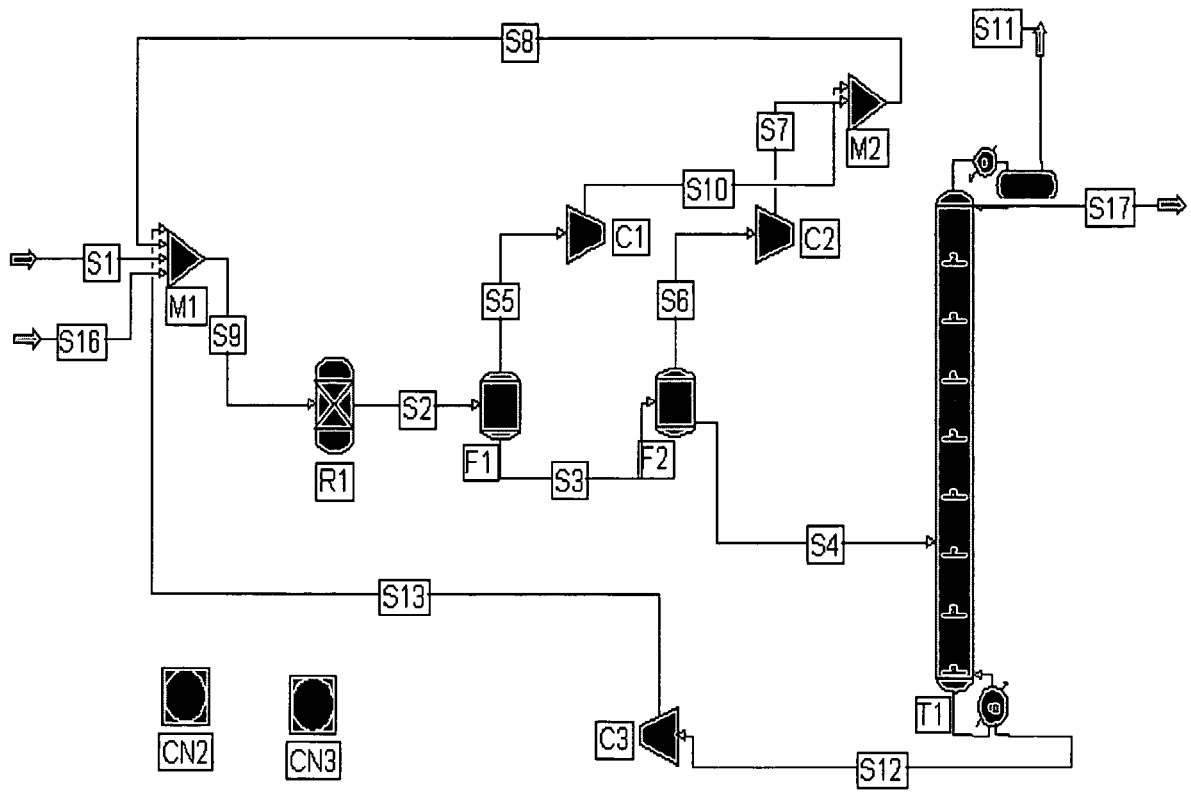
FIG. 2 depicts an exemplary process schematic of the process of the present invention for generating 1-hexene with toluene as a solvent.

Another exemplary process using toluene as the catalyst solvent is shown in FIG. 2. The ethylene feed S1 is again 100% ethylene while the reaction selectivity to 1-hexene is 100%. The ethylene feed S1 is mixed through M1 with recycle stream S8 containing ethylene, solvent, and 1-hexene and is fed to reactor R1. The reactor R1 is operated at 100° C. and 400 psia and is sized to achieve 50% per pass conversion of ethylene. The product and the solvent are separated from the unconverted ethylene using two flash drums F1, F2 in series operated at 300 and 14.96 psia respectively. The gas outlets of the flash drums S5, S6 are recompressed to 400 psia, combined in one stream S8 and recycled back to the reactor R1. The liquid stream S4 from flash unit F2 is fed to a distillation column operation T1 at atmospheric pressure in order to separate 1-hexene S17 from the toluene solvent S12. The toluene solvent S12 collected at the bottom of the column is recycled via S13. Since the homogeneous or slurry catalyst leaves with the solvent, a portion of that recycled stream can be purged and fresh catalyst added to the system via S16 such that the activity of the catalyst in the reactor can be maintained constant. A summary listing of stream flow rates and compositions is shown in Table 2. An increase in the ethylene conversion would allow further simplification of the process similar to that of example 1.

TABLE 2

Flow Rates and Compositions

|  | Rate (lb/hr) | Ethylene | Toluene | 1-Hexene |
|---|---|---|---|---|
| Ethylene Feed | 33700 | 100% |  |  |
| Solvent Feed | 100 |  | 100.00% |  |
| Recycle | 65800 | 76% | 4% | 20% |
| Solvent Recycle | 39700 |  | 95% | 5% |
| Product | 31000 | 0.12% | 0.38% | 99.50% |

Simulation Example 3

1-Hexene Product with Isopentane as a Solvent—High Pressure

Figure 3:
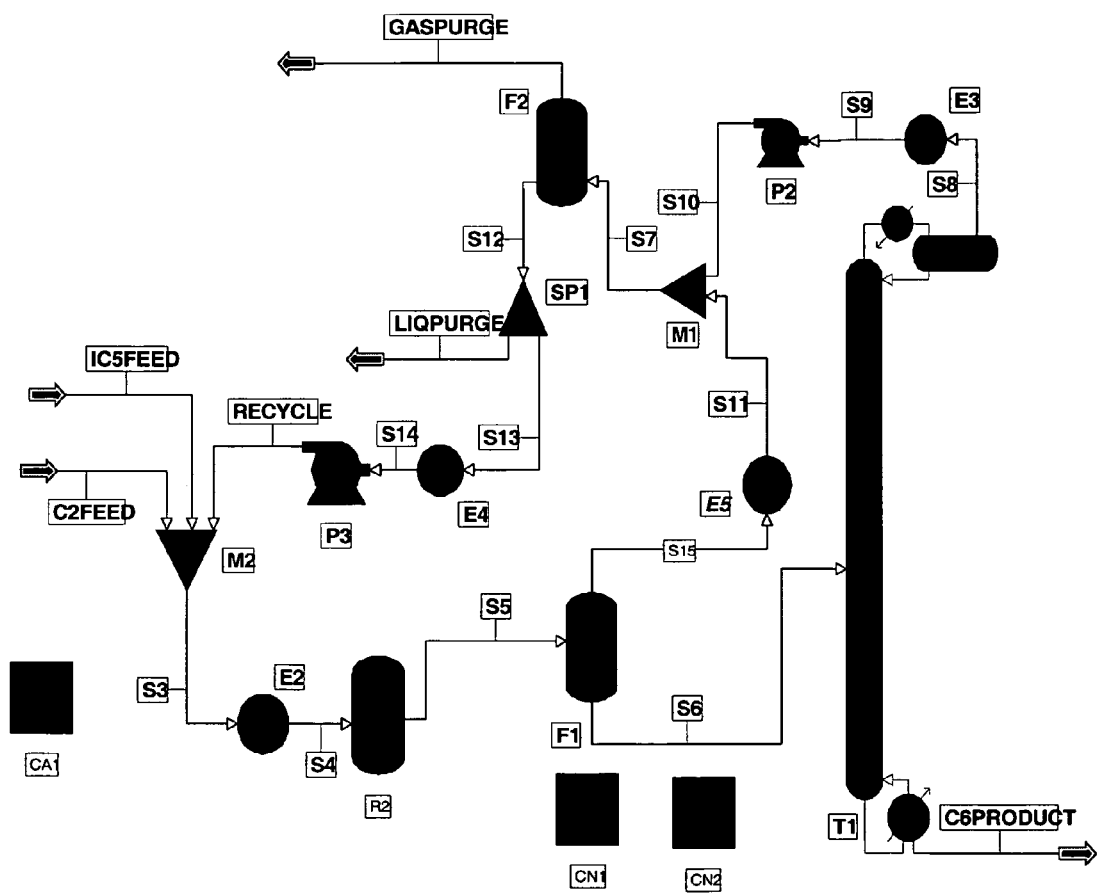
FIG. 3 depicts an exemplary process schematic of the process of the present invention for generating 1-hexene with isopentane as a solvent at high pressure.

Another exemplary process using isopentane as the catalyst solvent at high pressure is shown in FIG. 3. Increasing the process pressure allows for an operation with the recycle stream as a liquid, which permits the use of a pump instead of an expensive compressor to transport the recycle stream. In this exemplary process, ethylene feed (C2FEED) is oligomerized to 1-hexene at 90° C. and 800 psia using isopentane, IC5FEED, as a catalyst solvent. The C2FEED is 100% ethylene while the reaction selectivity to 1-hexene is 100%. The feed is mixed with recycled ethylene, isopentane and 1-hexene (Recycle) and fed to the reactor R2. The reactor R2 is operated at 90° C. and 800 psia and is sized to achieve 80% per pass conversion of ethylene. The reactor product stream S5 is then fed to a flash drum F1 where the 1-hexene stream S6 is separated from the unconverted ethylene and catalyst solvent stream S15 at 150 psia. The bottoms stream S6 from the flash drum F1 is then fed to a distillation column T1 operated at 60 psia to complete the separation of 1-hexene, C6PRODUCT, from unconverted ethylene and catalyst solvent S8. The C6PRODUCT, including the homogeneous/slurry catalyst, is collected at the bottom of the distillation column. The overhead vapors of unconverted ethylene and catalyst solvent S8 from the distillation column T1 are condensed to form a liquid stream S9 using a heat exchanger E3 and transported using a pump P2 operated at 150 psia. The condensed unconverted ethylene and catalyst solvent stream S10 and a condensed overhead vapor stream S11 from the from the flash drum F1 are mixed through a mixing element M1. The combined stream S7 is separated into a gas and liquid phase in second flash drum F2. The liquid stream S13 is then subcooled through a heat exchanger E4, pumped back to 800 psia using a pump P3 and recycled back to the reactor R2 as a recycle stream (RECYCLE). A summary listing of stream flow rates and compositions is shown in Table 3.

TABLE 3

Flow Rates and Compositions

|  | Rate (lb/hr) | Ethylene | Isopentane | 1-Hexene |
|---|---|---|---|---|
| Ethylene Feed | 33700 | 100% |  |  |
| Solvent Feed | 142 |  | 100.00% |  |
| Recycle | 50428 | 34% | 63% | 3% |
| Product | 33700 | 0.00% | 0.50% | 99.50% |

Simulated Example 4

1-Butene Product with Isopentane as a Solvent—High Pressure

Figure 4:
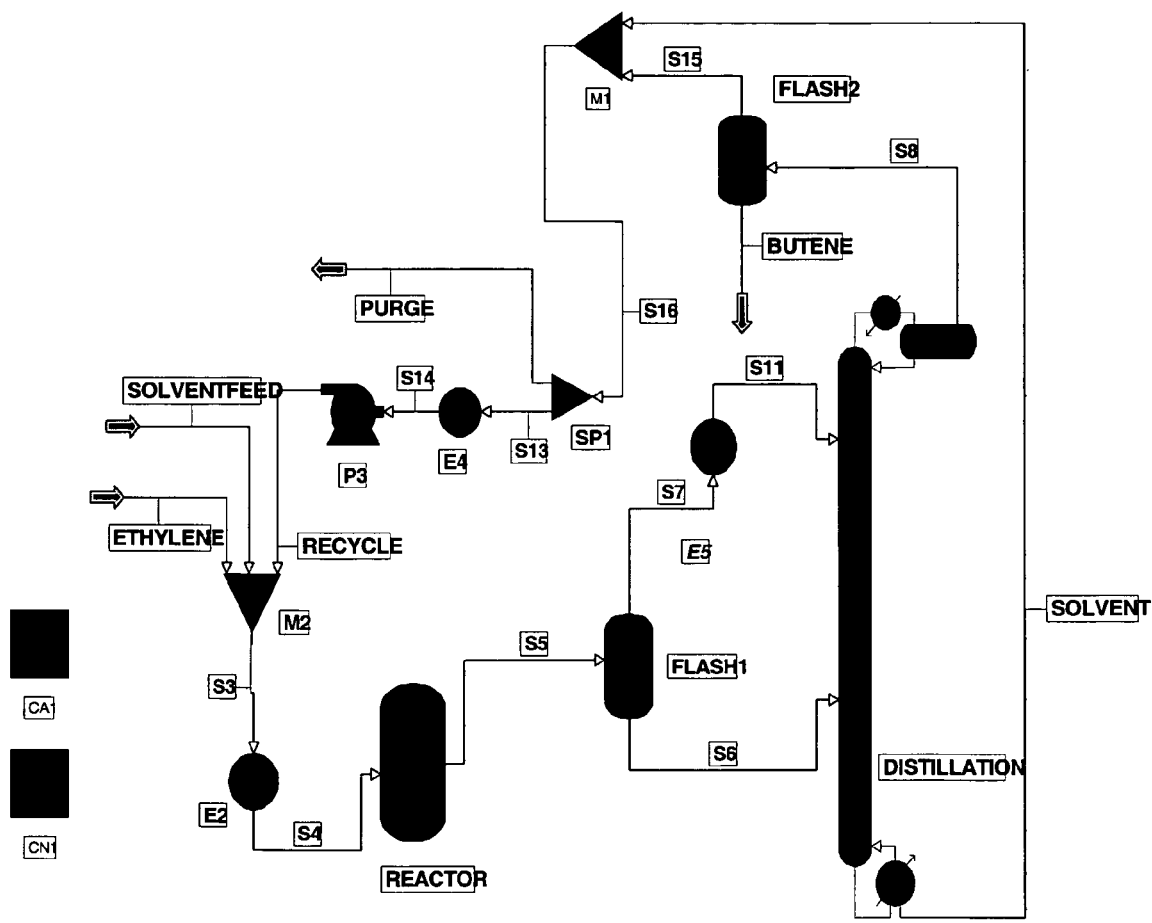
FIG. 4 depicts an exemplary process schematic of the process of the present invention for generating 1-butene with isopentane as a solvent at high pressure.

Another exemplary process to produce 1-butene using isopentane as the catalyst solvent at high pressure is shown in FIG. 4. In this example, the conditions and the process flow schematic are similar to Example 3. However, instead of a 1-hexene selective catalyst, a 1-butene selective catalyst is used. 1-butene is lighter than isopentane and is collected as the overhead vapor S8 from the distillation column operating at 60 psia. The vapors, which are a mixture of 1-butene and ethylene are then cooled to −20° C., and the liquid product is separated in a second flash drum, FLASH2, operating at 50 psia. The product stream, BUTENE, from the second flash drum, FLASH2, is 85.5% 1-butene. This product stream, BUTENE, can be directly fed to a polyethylene reactor (not shown). However if a higher purity is needed a second distillation column instead of the second flash drum, FLASH2, may be used. The overhead vapors from the second flash drum, FLASH2, are mixed through a mixing device M1 with the recycled isopentane stream from the distillation column, SOLVENT, condensed through a heat exchanger, E4, and pumped with a pump P3 to 800 psia, and then recycled as a recycle stream (RECYCLE) to the reactor. A summary listing of stream flow rates and compositions is shown in Table 4.

TABLE 4

Flow Rates and Compositions

|  | Rate (lb/hr) | Ethylene | Isopentane | 1-Butene |
|---|---|---|---|---|
| Ethylene Feed | 33700 | 100% | | |
| Solvent Feed | 308 | | 100.00% | |
| Recycle | 47072 | 24.20% | 70.90% | 4.90% |
| Product | 34008 | 14.50% | 0.00% | 85.50% |

Simulated Example 5

1-Hexene Product with Toluene Solvent w/Polymer Grade Feed

Figure 5:
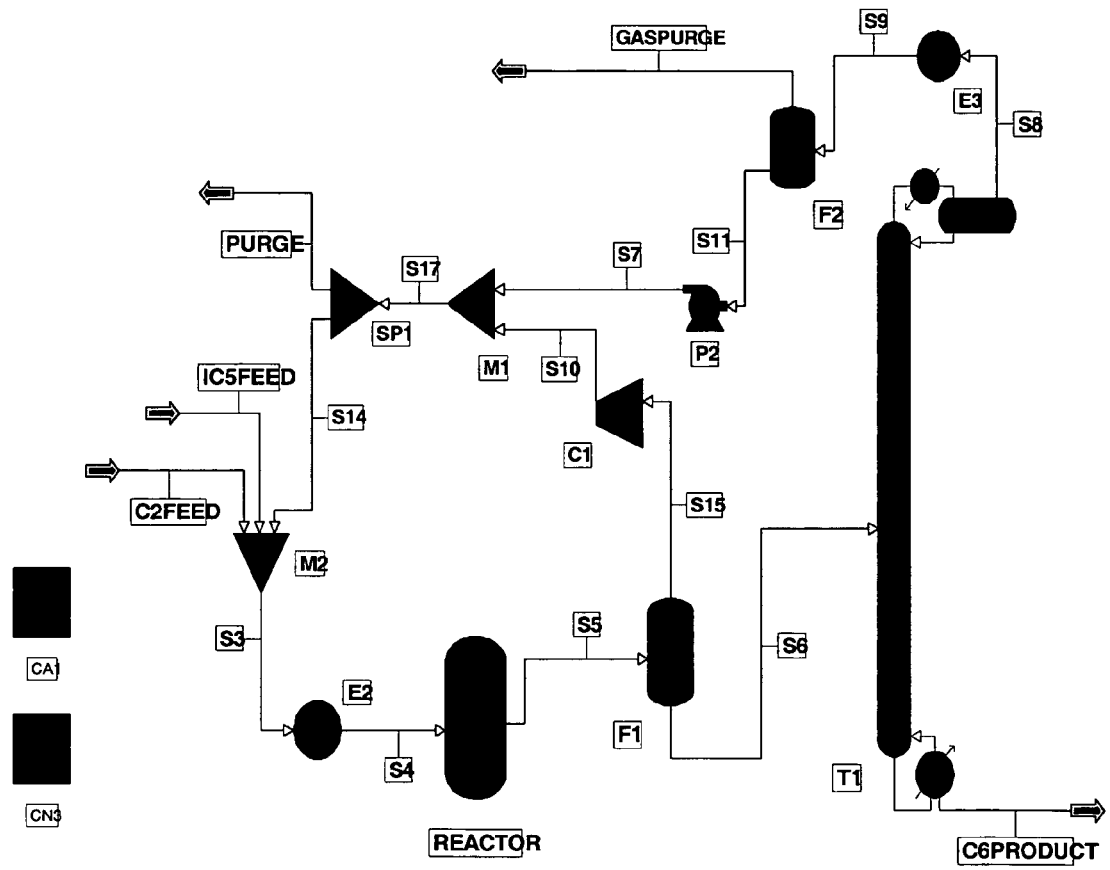
FIG. 5 depicts an exemplary process schematic of the process of the present invention for generating 1-hexene with isopentane as a solvent and using polymer grade feed.

Another exemplary process to produce 1-hexene using isopentane as the catalyst solvent with a polymer grade ethylene feed is shown in FIG. 5. The ethylene feed, C2FEED, is 99.9% ethylene and 0.1% ethane (polymer grade feed) while the reaction selectivity to 1-hexene is 98% 1-hexene, 0.4% 1-octene and 1.6% decenes (both 1-decene and internals). The feed is mixed through a mixing device M2 with recycled ethylene S14 and isopentane IC5FEED and fed to the reactor. The reactor is operated at 90° C. and 400 psia and is sized to achieve 80% per pass conversion of ethylene. The product stream from the reactor S5 is separated from unconverted ethylene using a flash drum F1 operated at 200 psia. The gas outlet S15 of the flash drum F1 is then recompressed through a compressor C1 at 400 psia and recycled. The liquid stream S6 from the flash drum F1 is fed to a distillation column T1 operating at 60 psia. At the bottom of the distillation column 1-hexene and the heavier alpha-olefins are collected as the product stream from the column C6PRODUCT. The overhead vapors from the column S8 are then cooled at 0° C. using a heat exchanger E3 and conveyed to a second flash drum F2. The liquid phase S11 from the second flash drum F2 containing mostly ethylene is pumped using a pump P2 to 400 psia and recycled back to the reactor. The gas phase, GASPURGE, is purged from the second flash drum F2. Homogeneous or slurry catalyst leaves with the 1-hexene product, C6PRODUCT. A summary listing of stream flow rates and compositions is shown in Table 5.

TABLE 5

Flow Rates and Compositions

|  | Rate (lb/hr) | Ethylene | Isopentane | 1-hexene | 1-octene | Decenes | Ethane |
|---|---|---|---|---|---|---|---|
| Ethylene Feed | 33700 | 99.9% | | | | | 0.1% |
| Solvent Feed | 2230 | | 100.00% | | | | |
| Recycle | 28169 | 41.14% | 53.57% | 4.55% | | | 0.74% |
| Product | 31632 | 0.00% | 0.29% | 98.41% | 0.30% | 1.00% | |

What is claimed is:

1. A method for preparing linear alpha olefin comonomers from ethylene monomer comprising the following steps:
    providing one or more comonomer synthesis reactors configured in series, and one or more downstream gas/liquid phase separators configured in series;
    feeding an ethylene monomer, and a catalyst in a solvent to said one or more comonomer synthesis reactors;
    reacting in said one or more comonomer synthesis reactors said ethylene monomer and said catalyst in solvent under reaction conditions to produce an effluent stream comprising unreacted ethylene monomer, said catalyst in a solvent, and comonomer;
    passing said effluent stream to said one or more downstream gas/liquid phase separators to form a gas stream of said unreacted ethylene monomer, and a liquid stream of said comonomer and said catalyst in a solvent;
    recycling to said one or more comonomer synthesis reactors said unreacted ethylene monomer and a portion of said liquid stream; and
    storing a remaining portion of said liquid stream for subsequent processing of said comonomer;
    wherein said comonomer is selected from the group consisting of 1-butene, 1-octene, 1-decene and mixtures thereof, and said comonomer is said solvent.

2. The method of claim 1, wherein said comonomer is used in a polyethylene polymerization reactor.

3. The method of claim 1, wherein said one or more comonomer synthesis reactors are a stirred tank reactor, a long, thin tube-like contactor, or a bubble column type reactor.

4. The method of claim 1, wherein said ethylene monomer is greater than about 99% ethylene.

5. The method of claim 1, wherein said catalyst is selected from the group consisting of a chromium trimerization catalyst, a vanadium trimerization catalyst, a tantalum trimerization catalyst, a titanium trimerization catalyst, a chromium tetramerization catalyst, a vanadium tetramerization catalyst, a tantalum tetramerization catalyst, and a titanium tetramerization catalyst.

6. The method of claim 1, wherein said catalyst further comprises one or more organic ligands, one or more inorganic ligands, one or more activators, or mixtures thereof.

7. The method of claim 1, wherein said reaction conditions yield from about 40% to about 95% conversion of said ethylene monomer.

8. The method of claim 7, wherein said reaction conditions yield from about 60% to about 90% conversion of said ethylene monomer.

9. The method of claim 7, wherein said reaction conditions comprise a reaction temperature from about 80 to about 150° C., a reaction pressure from about 300 to about 900 psi, and a reaction residence time from about 30 minutes to about 4 hours.

10. The method of claim 1, wherein a catalyst deactivator is added to said effluent stream exiting from said one or more comonomer synthesis reactors, wherein said catalyst deactivator is water or alcohol.

11. The method of claim 1, wherein said one or more downstream gas/liquid phase separators comprise a knockout vessel, a flash drum, or a stirred tank or pot.

12. The method of claim 11, wherein said one or more downstream gas/liquid phase separators further comprise trays or packing in the vapor zone.

13. The method of claim 1 further comprising the step of adding ethylene monomer to said one or more downstream gas/liquid phase separators to strip out comonomer from said liquid stream.

14. A method for preparing linear alpha olefin comonomers from ethylene monomer comprising the following steps:
providing one or more comonomer synthesis reactors configured in series, one or more downstream gas/liquid phase separators configured in series, and one or more distillation columns configured in series;
feeding an ethylene monomer, and a catalyst in a solvent to said one or more comonomer synthesis reactors;
reacting in said one or more comonomer synthesis reactors said ethylene monomer and said catalyst in solvent under reaction conditions to produce an effluent stream comprising unreacted ethylene monomer, said catalyst in a solvent, and comonomer;
passing said effluent stream to said one or more downstream gas/liquid phase separators to form a gas stream of said unreacted ethylene monomer, and a liquid stream of said comonomer and said catalyst in a solvent;
passing said liquid stream of said comonomer and said catalyst in a solvent to said one or more distillation columns to separate said comonomer from said catalyst in a solvent;
recycling to said one or more comonomer synthesis reactors said unreacted ethylene monomer and said catalyst in a solvent; and
storing said comonomer for subsequent processing;
wherein said comonomer is selected from the group consisting of 1-butene, 1-octene, 1-decene and mixtures thereof, and said comonomer is said solvent.

15. The method of claim 14, wherein said comonomer is used in a polyethylene polymerization reactor.

16. The method of claim 14, wherein said one or more comonomer synthesis reactors are a stirred tank reactor, a long, thin tube-like contactor, or a bubble column type reactor.

17. The method of claim 14, wherein said ethylene monomer feed is greater than about 99% ethylene.

18. The method of claim 14, wherein said catalyst is selected from the group consisting of a chromium trimerization catalyst, a vanadium trimerization catalyst, a tantalum trimerization catalyst, a titanium trimerization catalyst, a chromium tetramerization catalyst, a vanadium tetramerization catalyst, a tantalum tetramerization catalyst, and a titanium tetramerization catalyst.

19. The method of claim 14, wherein said catalyst further comprises one or more organic ligands, one or more inorganic ligands, one or more activators, or mixtures thereof.

20. The method of claim 14, wherein said reaction conditions yield from about 40% to about 95% conversion of said ethylene monomer.

21. The method of claim 20, wherein said reaction conditions yield from about 60% to about 90% conversion of said ethylene monomer.

22. The method of claim 20, wherein said reaction conditions comprise a reaction temperature from about 80 to about 150° C., a reaction pressure from about 300 to about 900 psi, and a reaction residence time from about 30 minutes to about 4 hours.

23. The method of claim 14, wherein a catalyst deactivator is added to said effluent stream exiting from said one or more comonomer synthesis reactors, wherein said catalyst deactivator is water or alcohol.

24. The method of claim 14, wherein said one or more downstream gas/liquid phase separators comprises a knockout vessel, a flash drum, or a stirred tank or pot.

25. The method of claim 24, wherein said one or more downstream gas/liquid phase separators further comprises trays or packing in the vapor zone.

26. The method of claim 14, further comprising the step of adding ethylene monomer to said one or more downstream gas/liquid phase separators to strip out comonomer from said liquid stream.

27. The method of claim 14, wherein said one or more distillation columns separate said catalyst in solvent from the top and said comonomer from the bottom.

28. The method of claim 27, wherein said one or more distillation columns further separate residual ethylene monomer from the top.

29. The method of claim 27, wherein said one or more distillation column is a divided wall type column.

30. The method of claim 14, wherein said one or more distillation column separate said comonomer from the top and said catalyst in solvent from the bottom.

31. A method for preparing linear alpha olefin comonomers from ethylene monomer comprising the following steps:
providing a combination comonomer synthesis reactor and gas/liquid phase separator into a single vessel;
feeding an ethylene monomer, and a catalyst in a solvent to said combination comonomer synthesis reactor and gas/liquid phase separator;
reacting in said combination comonomer synthesis reactor and gas/liquid phase separator said ethylene monomer and said catalyst in solvent under reaction conditions to produce an effluent stream comprising a gas stream of unreacted ethylene monomer and a liquid stream of comonomer and catalyst in a solvent;

recycling to said combination comonomer synthesis reactor and gas/liquid phase separator said gas stream and a portion of said liquid stream; and storing a remaining portion of said liquid stream for subsequent processing of said comonomer;

wherein said comonomer is at least one of 1-butene, 1-octene and 1-decene and mixtures thereof, and said comonomer is said solvent.

32. The method of claim 31, wherein said comonomer is used in a polyethylene polymerization reactor.

33. The method of claim 31, wherein said ethylene monomer feed is greater than about 99% ethylene.

34. The method of claim 31, wherein said catalyst is selected from the group consisting of a chromium trimerization catalyst, a vanadium trimerization catalyst, a tantalum trimerization catalyst, a titanium trimerization catalyst, a chromium tetramerization catalyst, a vanadium tetramerization catalyst, a tantalum tetramerization catalyst, and a titanium tetramerization catalyst.

35. The method of claim 31, wherein said catalyst further comprises one or more organic ligands, one or more inorganic ligands, one or more activators, or mixtures thereof.

36. The method of claim 31, wherein said reaction conditions yield from about 40% to about 95% conversion of said ethylene monomer.

* * * * *